United States Patent [19]

Berkowitz

[11] 4,147,720

[45] Apr. 3, 1979

[54] PROCESS FOR PREPARING ALIPHATIC DIPEROXYDICARBOXYLIC ACIDS

[75] Inventor: Sidney Berkowitz, Highland Park, N.J.

[73] Assignee: FMC Corporation, Philadelphia, Pa.

[21] Appl. No.: 866,091

[22] Filed: Dec. 30, 1977

[51] Int. Cl.$^2$ .......................................... C07G 179/10
[52] U.S. Cl. ............................................... 260/502 R
[58] Field of Search ............ 260/502 R, 610 D, 502 A

[56] References Cited

U.S. PATENT DOCUMENTS

| | | | |
|---|---|---|---|
| 2,813,896 | 11/1957 | Krimm | 260/502 R |
| 3,264,346 | 9/1966 | Weiberg | 260/502 R |
| 3,284,491 | 11/1966 | Korach | 260/502 R |

FOREIGN PATENT DOCUMENTS

| | | | |
|---|---|---|---|
| 744391 | 10/1966 | Canada | 260/502 R |
| 745594 | 2/1956 | United Kingdom | 260/502 R |
| 975715 | 11/1964 | United Kingdom | 260/502 R |

*Primary Examiner*—Werren B. Lone
*Attorney, Agent, or Firm*—Christine M. Miles; Frank Ianno

[57] ABSTRACT

Saturated $C_6$–$C_{16}$ aliphatic diperoxydicarboxylic acids are prepared in a safe and efficient manner by reacting a selected corresponding dicarboxylic acid and hydrogen peroxide in a phosphoric acid reaction medium at a temperature within the range of from about 20° to about 70° C.

44 Claims, No Drawings

PROCESS FOR PREPARING ALIPHATIC DIPEROXYDICARBOXYLIC ACIDS

The present invention relates to the production of aliphatic peroxycarboxylic acids, and more particularly, to the production of saturated $C_6$–$C_{16}$ aliphatic diperoxydicarboxylic acids.

Aliphatic peroxycarboxylic acids are well known and have long been used, for example, as catalysts, oxidizing agents, bleaching agents, and disinfecting agents, the diperoxydicarboxylic acids in particular, possessing superior oxidizing, bleaching and disinfecting properties.

Organic peroxyacids were first prepared by J. D'Ans during the early path of the twentieth century. German Pat. No. 251,802, issued Sept. 7, 1911, to J. D'Ans describes and the preparation of $C_1$–$C_4$ monobasic peroxycarboxylic acids by reacting the corresponding carboxylic acid or acid anhydride with concentrated hydrogen peroxide (about 95%) in the presence of a small amount of catalyst, e.g., 1% sulfuric acid (calculated on the hydrogen peroxide). The reaction so described is strongly exothermic, often increasing spontaneously to explosive violence. The process is less suitable for the preparation of aliphatic peroxyacids having 6 or more carbon atoms due to the low solubility of the parent acid in aqueous hydrogen peroxide, which prevents intimate contact between the reactants and causes the reaction to proceed at a very slow rate.

Parker has described a process for the preparation of long chain, aliphatic peroxyacids involving reacting the corresponding carboxylic acid with 50-65% hydrogen peroxide in concentrated sulfuric acid. J. Am. Chem. Soc. 77, 4037-41 (1955). The application of this reaction to the preparation of long chain aliphatic diperoxydicarboxylic acids is also described by Parker. J. Am. Chem. Soc. 79, 1929-1931 (1957). This latter process requires careful temperature control, generally within the range of 20°-25° C. in order to minimize the hazard of explosion. This hazard is particularly accentuated when the process is scaled up to industrial production levels, where the ability to effect rapid heat exchange essential for safe operation is more difficult.

Silbert et al replaced the sulfuric acid of the Parker processes described above, with methanesulfonic acid, which, because of its lower oxidation potential and higher solvation capacity, at a comparable strength to sulfuric acid, overcomes many of the problems presented by use of a sulfuric acid reaction medium (e.g., low solvation in sulfuric acid of dibasic acids greater than $C_{12}$ and decomposition of aromatic acids and compounds with functional groups sensitive to sulfuric acid). J. Org. Chem. 27, 1336-42 (1962). However, methanesulfonic acid is a very expensive chemical, and its use does not provide an economical process for the preparation of diperoxydicarboxylic acids.

U.S. Pat. No. 2,813,896, to Krimm, describes inter alia a purportedly safe process for the preparation of two diperoxydicarboxylic acids, namely diperadipic acid (a $C_6$ acid) and dipersebacic acid (a $C_{10}$ acid). The process involves employing sulfuric acid in amounts such that the molar ratio of sulfuric acid to water is at least 1 to 6 at the end of the reaction. The reaction rates are slow, requiring an overnight reaction period before these diperoxyacids are obtained in good yields. The preparation of longer chain diperoxyacids by the disclosed process would appear to require even longer reaction times.

M. Korach, in U.S. Pat. No. 2,877,266, discloses a process for the preparation of peroxyacids, including diperoxydicarboxylic acids, which involves reacting the corresponding carboxylic acid with concentrated hydrogen peroxide in a liquid phase containing an inert solvent which forms an azeotrope with water. The reaction is driven to completion by azeotropic distillation of said solvent and water from the liquid phase. M. Korach, et al subsequently disclose in U.S. Pat. No. 3,284,491, a process designed to reduce the hazard of explosion inherent in the process described in U.S. Pat. No. 2,877,266. The new process involves employing enough of a water miscible solvent to permit all of the liquids in the reaction mixture undergoing distillation to form a single liquid phase. The process described by this patent, however, entails a costly distillation procedure, and organic vapors arising therefrom would require complex recovery procedures to prevent a potential pollution problem. Further, the water miscible solvents used in the process are generally difficult to remove from the final product.

It is an object of this invention to provide a safe and economical process for the preparation of saturated $C_6$–$C_{16}$ aliphatic diperoxydicarboxylic acids.

Additional objects and advantages of the present invention will become apparent from the following description and the appended claims.

According to the invention, a saturated $C_6$–$C_{16}$ aliphatic diperoxydicarboxylic acid is prepared by a process which comprises the steps of bringing together and reacting, a saturated $C_6$–$C_{16}$ aliphatic dicarboxylic acid and hydrogen peroxide in a phosphoric acid reaction medium in a reaction zone, wherein the molecular ratio of said dicarboxylic acid and hydrogen peroxide is within the range of from about 1:2 to about 1:5, whereby there is formed a reaction slurry in said reaction zone; maintaining the reaction slurry in an agitated condition; maintaining the temperature of the reaction slurry within the range of from about 20° to about 70° C. during the reaction period and thereafter separating the diperoxydicarboxylic acid from the reaction slurry.

The formation of a peroxyacid from a carboxylic acid and hydrogen peroxide is an equilibrium process, which proceeds in accordance with the following overall equation, where R is an organic moiety:

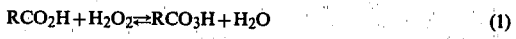

$$RCO_2H + H_2O_2 \rightleftharpoons RCO_3H + H_2O \quad (1)$$

Further, the formation of aliphatic peroxyacids is acid catalyzed according to the following equations, where R is an organic moiety:

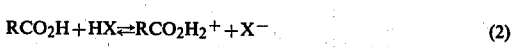

$$RCO_2H + HX \rightleftharpoons RCO_2H_2^+ + X^- \quad (2)$$

$$RCO_2H_2^+ + H_2O_2 \rightleftharpoons RCO_3H + H_3O^+ \quad (3)$$

In carrying out the process of the invention, the above reactions are effected between a saturated $C_6$–$C_{16}$ aliphatic dicarboxylic acid and hydrogen peroxide by employing phosphoric acid as the reaction medium, under the reaction conditions and parameters described below. The preferred aliphatic dicarboxylic acids are those having 6 to 12 carbon atoms. The phosphoric acid reaction medium serves as both a mutual solvent for the reactants and as a catalyst for the reaction.

Although the concentration of the phosphoric acid employed may vary, the reaction rate has been found to be particularly sensitive to such concentration. Good yields of diperoxydicarboxylic acids are obtained at phosphoric concentrations within the preferred range of from about 70 to about 100% by weight. Maximum yields are obtained at concentrations within the range of from about 85 to about 95%, which constitutes the most preferred range of phosphoric acid concentration.

The amount of phosphoric acid employed may likewise be varied. Molar ratios of dicarboxylic acid to phosphoric acid within the range from about 1:6 to about 1:15 have been found entirely satisfactory in carrying out the process of the invention, the most preferred range being from about 1:8 to about 1:12. Preferably the amount of phosphoric acid is sufficient to provide an easily stirrable reaction mixture in order to facilitate effectuation of adequate heat exchange in the reaction slurry. As it is additionally preferred to predissolve the dicarboxylic acid reactant in the phosphoric acid reaction medium (generally at elevated temperatures on the order of 60°-100° C.) to promote a more intimate and uniform contact between the reactants, it is preferred to employ an amount of phosphoric acid which is also sufficient to effect such predissolution.

Where a dicarboxylic acid reactant having 12 or more carbon atoms is employed, the reaction is preferably further catalyzed by addition of a small amount of a stronger acid (100% concentration basis), i.e., up to about 5% of the phosphoric acid. Suitable stronger acids include for example, sulfuric acid, methanesulfonic acid, trifluoromethanesulfonic acid, and toluenesulfonic acid. Such further catalysis is preferred as the reaction time tends to increase with increasing chain length of the dicarboxylic acid reactant.

The hydrogen peroxide reactant used may vary in concentration within the range of from about 30% to about 90% by weight. Concentrations of at least about 65% up to 90% are most preferred, in order to minimize dilution of the reaction mixture with water, and thereby give good conversions to product.

The amount of hydrogen peroxide used in the reaction may likewise be varied, although in order to achieve complete conversion of the dicarboxylic acid to the corresponding diperoxydicarboxylic acid, at least two moles of hydrogen peroxide per mole of dicarboxylic acid reactant are necessary according to the following equation:

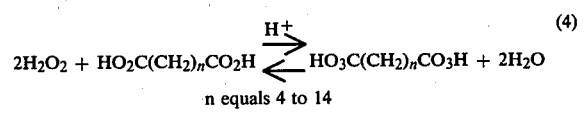

$$2H_2O_2 + HO_2C(CH_2)_nCO_2H \underset{\longleftarrow}{\overset{H^+}{\longrightarrow}} HO_3C(CH_2)_nCO_3H + 2H_2O \quad (4)$$

n equals 4 to 14

Molar ratios of dicarboxylic acid to hydrogen peroxide within the range of from about 1:2 to about 1:5 are preferred. Optimum conversions to product with optimum utilization of the hydrogen peroxide, have been obtained at dicarboxylic acid to hydrogen peroxide ratios within the range of from about 1:3 to about 1:4.

In general, according to the preferred procedure for carrying out the process of the invention, the dicarboxylic acid reactant is predissolved in the phosphoric acid media as described above, and if necessary, cooled to the reaction temperature. Suitable reaction temperatures are within the range of from about 20° to about 70° C., preferred range being from about 40° to about 60° C.

The hydrogen peroxide reactant is added to the reaction medium containing the dicarboxylic acid reactant preferably at a rate sufficient to maintain the reaction temperature. If a faster addition rate is desired, cooling may be supplied to control the reaction temperature. Means are provided for maintaining the resulting reaction slurry in an agitated condition to facilitate contact between the reactants, to effectuate adequate heat exchange in said slurry and to help carry out the reaction within the above temperature range. Minimal cooling may be necessary to control the reaction temperature, particularly where temperatures at the lower end of the 20°-70° C. temperature range are employed.

The reaction time for obtaining good yields of diperoxydicarboxylic acid product can vary from less than an hour to several hours, the time being a function of several parameters, most importantly, phosphoric acid concentration, reaction temperature, chain length of the dicarboxylic acid reactant and rate of stirring of the reaction slurry. As might be expected, increasing all of the above parameters except chain length of the dicarboxylic acid reactant decreases the reaction time.

A diperoxydicarboxylic acid product precipitates in the reaction mass resulting in a reaction slurry. The acid is typically separated by filtering (or centrifuging or the like) the slurry. It is preferred to cool the slurry to a temperature on the order of 5° to 20° C. to precipitate addtional amounts of product before separation by filtration or the like. The separated product is preferably washed with water to remove additional amounts of phosphoric acid and hydrogen peroxide therefrom, and dried. The presence of residual amounts of phosphoric acid, on the order of 1 to 2% on the product, however, can be tolerated without adversely affecting the stability of the product. Such residual amounts of sulfuric acid by contrast, cannot be so tolerated without degradation of the diperoxydicarboxylic acid product.

The above described process can be carried out in either a batch or continuous fashion, as desired. When the process is carried out in batch fashion however, it is preferred that the hydrogen peroxide be added to the phosphoric acid reaction medium after addition of the dicarboxylic acid reactant. In a continuous process the reactants are fed continuously to a reactor to form the acid product, and a portion of the resulting slurry is removed continuously and treated by filtration or the like to separate the product; the resulting mother liquor separated during filtration can then be recycled to the reactor.

The following examples are given to illustrate the invention and are not intended to be limiting thereof.

EXAMPLE I

Run A — Example of the Invention

This run demonstrates the safety factor inherent in using phosphoric acid as the reaction medium for the production of diperoxyazelaic acid. Nine and four tenths grams (0.05 moles) of azelaic acid (assay 99+%) were added to 60 grams (0.58 moles) of phosphoric acid (95% assay) in a 250 ml tall-form beaker equipped with a thermometer, liquid charging funnel and a Teflon ® coated mechanical stirrer. A suspension formed in the beaker, and was heated to 90° C., completely dissolving the azelaic acid. The solution was cooled to essentially the reaction temperature of 45° C., and 9.12 grams (0.25 moles) of hydrogen peroxide (70% assay) were added dropwise thereto over a period of 3–4 minutes. A white precipitate began to separate from the solution during the hydrogen peroxide addition and the reaction temperature increased by 5° C. After addition of hydrogen peroxide was completed, the reaction mixture, which became a thick slurry, was stirred for 50 minutes at a temperature of 45°-50° C., then cooled to 15° C. and filtered. The filtered solids were washed to removed residual phosphoric acid and hydrogen peroxide and dried at 30° C./20 Torr. The total solids recovered from the reaction mixture were identified as essentially pure, diperoxyazelaic acid by melting point, X-ray diffraction and active oxygen analyses. The total yield was 10.5 grams which is the equivalent of essentially 95% based on the starting azelaic acid.

Run B — Comparative Example

This run demonstrates the potential danger in using sulfuric acid as the reaction medium for the production of diperoxyazelaic acid. Nine and four tenths grams (0.05 moles) of azelaic acid (assay 99+%) were added to 59.2 grams (0.58 moles) of sulfuric acid (96% assay) in a beaker as described in Run A above. A suspension formed in the beaker and was heated to 60° C., completely dissolving the azelaic acid. The solution was cooled to essentially the reaction temperature of 25° C. and 9.12 grams (0.02 moles) of hydrogen peroxide (70% assay) were added dropwise thereto over a period of 3-4 minutes. A white precipitate began to separate from the solution during the hydrogen peroxide addition. The reaction became exothermic. Attempts to control the exotherm with external cooling were unsuccessful. The temperature rose rapidly and exceeded 140° C., at which point the reaction mass exploded out of the beaker, spraying hot acid, and charred organics about the area of the reaction.

Example II below demonstrates the further catalytic effect of small amounts of a stronger acid, in the phosphoric acid reaction medium, in the production of aliphatic diperoxydicarboxylic acids having chain lengths of $C_{12}$ and greater. In Example II, a small amount of sulfuric acid was added to the phosphoric acid reaction medium. In Example III a similar run was made to Example II except that no additional acid catalyst was used, and the reaction was carried out for five hours, instead of one hour as in Example II.

EXAMPLE II

Eleven and six tenths grams (0.05 moles) of dodecanedioic acid (assay 99+%) were added to a solution containing 40.0 grams (0.39 moles) of phosphoric acid (95% assay) and 1.0 gram (0.009 moles) of sulfuric acid (96% assay) in a beaker as described in Run A of Example I. A suspension formed in the beaker and was heated to 90° C., completely dissolving the dodecanedioic acid. The solution was cooled to essentially the reaction temperature of 50° C., and 7.3 grams (0.15 moles) of hydrogen peroxide (70% assay) were added dropwise thereto over a period of 3-4 minutes. There was no detectable exotherm. After the addition of hydrogen peroxide was completed, the reaction mixture, which became a thick slurry, was stirred for one hour at a temperature of 50° C., then diluted with an equivalent amount of water, and filtered. The filtered solids were washed with water. The yield of diperoxydodecanedioic acid as determined by active oxygen analysis was 1.01 grams, which is the equivalent of 10.1% based on the starting dodecanedioic acid.

EXAMPLE III

Eleven and six tenths grams (0.05 moles) of dodecanedioic acid (assay 99+%) were added to 41.26 grams (0.40 moles) of phosphoric acid (assay 95%) in a beaker as described in Run A of Example I. A suspension formed in the beaker and was heated to 90° C., completely dissolving the dodecanedioic acid. The solution was cooled to essentially the reaction temperature of 50° C., and 7.3 grams (0.15 moles) of hydrogen peroxide (70% assay) were added dropwise thereto over a period of 3-4 minutes. There was no detectable exotherm. After the addition of the hydrogen peroxide was completed, the reaction mixture, which became a thick slurry, was stirred for six hours at a temperature of 50° C., then diluted with an equivalent amount of water and filtered. The filtered solids were washed with water. The yield of diperoxydodecanedioic acid as determined by active oxygen analysis was 0.82 grams, which is equivalent to 6.0% based on the starting dodecanedioic acid.

EXAMPLE IV

This example demonstrates that low reaction temperatures (requiring longer reaction times), if desired, may be employed in the process of the invention. Nine and four tenths grams (0.05 moles) of azelaic acid (assay 99+%) were added to 40.0 grams (0.4 moles) of phosphoric acid (95% assay) in a beaker as described in Example 1. A suspension formed in the beaker and was heated to 90° C., completely dissolving the azelaic acid. The solution was cooled to essentially the reaction temperature of 25° C. and at this temperature, small crystals of azelaic acid crystallized out of the solution. Nine and seventy-one hundredths grams (0.2 moles) of hydrogen peroxide (70% assay) were added dropwise over a period of 5 minutes. A white precipitate began to separate from the solution during the hydrogen peroxide addition, and the reaction temperature was maintained at about 25° C. with minimal cooling. After addition of hydrogen peroxide was completed, the reaction mixture, which became a thick slurry, was stirred for 3.5 hours at a temperature of 25° C., then filtered. The filtered solids were washed and dried as described in Example 1. The yield of diperoxyazelaic acid as determined by active oxygen analysis was 10.4 grams, which is the equivalent of 94.5% based on the starting azelaic acid.

EXAMPLE V

This example demonstrates the effect of phosphoric acid concentration on the reaction rate in the process of the invention. The same equipment, procedure and quantity of chemicals were employed as in Example IV, except that 46.5 grams (0.40 moles) of 85% phosphoric acid were used. A seven hour reaction time was necessary to achieve a conversion equivalent to that obtained in Example IV.

Examples VI and VII below illustrate the stability of an aliphatic diperoxydicarboxylic acid compound, as produced by the process of the invention, in a phosphoric acid medium at a temperature near the high end of the reaction temperature range for the process of the invention.

EXAMPLE VI

One gram (0.0037 moles) of diperoxydodecanedioic acid (98% assay) was added to 25 grams (0.217 moles)

of phosphoric acid (85% assay) in a 100 ml tall-form beaker, forming a slurry. The slurry was heated with stirring in a water bath to a temperature of 60° C. and cooled slowly to room temperature. The solids were recovered by filtration, then washed and dried. Based on active oxygen analysis, no decomposition had occurred.

EXAMPLE VII

Using the same procedure and a second sample of the diperoxydicarboxylic acid employed in Example VI, a slurry of 1 gram (0.0037 moles) of diperoxydodecanedioic acid (98% assay) in 25 grams (0.217 moles) of sulfuric acid (85% assay) was prepared and heated with stirring in a water bath. In a temperature of 45°–50° C. the mixture suddenly became exothermic and exploded, spraying hot acid and charred organic material about the area.

What is claimed is:

1. A process for preparing a saturated $C_6$–$C_{16}$ aliphatic diperoxydicarboxylic acid which comprises the steps of bringing together and reacting, a saturated $C_6$–$C_{16}$ aliphatic dicarboxylic acid and hydrogen peroxide in a phosphoric acid reaction medium in a reaction zone, wherein the molecular ratio of said dicarboxylic acid and hydrogen peroxide is within the range of from about 1:2 to about 1:5, whereby there is formed a reaction slurry in said reaction zone, the amount of phosphoric acid employed being sufficient to provide an easily stirrable reaction mixture and to predissolve the dicarboxylic acid reactant at temperatures between about 60°–100° C.; maintaining the reaction slurry in an agitated condition; maintaining the temperature of the reaction slurry within the range of from about 20° to about 70° C. during the reaction period and thereafter separating the diperoxydicarboxylic acid from the reaction slurry.

2. Process of claim 1 wherein the hydrogen peroxide has a concentration within the range of from about 30 to about 90%.

3. Process of claim 2 wherein the hydrogen peroxide has a concentration of at least about 65%.

4. Process of claim 1 wherein the molecular ratio of dicarboxylic acid and hydrogen peroxide is within the range of from about 1:3 to 1:4.

5. Process of claim 1 wherein the phosphoric acid has a concentration within the range of from about 70 to about 100%.

6. Process of claim 5 wherein the phosphoric acid has a concentration within the range of from about 85 to about 95%.

7. Process of claim 1 wherein the molecular ratio of the dicarboxylic acid and phosphoric acid is within the range of from about 1:6 to about 1:15.

8. Process of claim 7 wherein the molecular ratio of the dicarboxylic acid and phosphoric acid is within the range of from about 1:8 to about 1:12.

9. Process of claim 1 wherein the dicarboxylic acid is dissolved in the phosphoric acid reaction medium prior to being brought together and reacted with the hydrogen peroxide.

10. Process of claim 1 wherein the dicarboxylic acid reactant is azelaic acid.

11. Process of claim 1 wherein the dicarboxylic acid reactant is dodecanedioic acid.

12. A process for preparing a saturated $C_6$–$C_{16}$ aliphatic diperoxydicarboxylic acid which comprises the steps of bringing together and reacting, a saturated $C_6$–$C_{16}$ aliphatic dicarboxylic acid and hydrogen peroxide having a concentration within the range of from about 30% to about 90%, in a phosphoric acid reaction medium, in a reaction zone, wherein the molecular ratio of said dicarboxylic acid and hydrogen peroxide is within the range of from about 1:2 to about 1:5, the phosphoric acid having a concentration within the range of from about 70 to about 100%, the molecular ratio of dicarboxylic acid and phosphoric acid being within the range of from about 1:6 to about 1:15, whereby there is formed a reaction slurry in said reaction zone; maintaining the reaction slurry in an agitated condition; maintaining the temperature of the reaction slurry within the range of from about 20° to about 70° C. and thereafter separating the diperoxydicarboxylic acid from the reaction slurry.

13. Process of claim 12 wherein the hydrogen peroxide has a concentration of at least about 65%.

14. Process of claim 12 wherein the phosphoric acid has a concentration within the range of from about 85 to about 95%.

15. Process of claim 12 wherein the molecular ratio of dicarboxylic acid to phosphoric acid is within the range of from about 1:8 to about 1:12.

16. Process of claim 12 wherein the dicarboxylic acid is dissolved in the phosphoric acid reaction medium prior to being brought together and reacted with the hydrogen peroxide.

17. Process of claim 12 wherein the dicarboxylic acid reactant is azelaic acid.

18. Process of claim 12 wherein the dicarboxylic acid reactant is dodecanedioic acid.

19. A process for preparing a saturated $C_{12}$–$C_{16}$ aliphatic diperoxydicarboxylic acid which comprises the steps of bringing together and reacting, a saturated $C_{12}$–$C_{16}$ aliphatic dicarboxylic acid and hydrogen peroxide in a phosphoric acid reaction medium containing up to about 5% by weight of the phosphoric acid of a stronger acid selected from the group consisting of sulfuric acid, methanesulfonic acid, trifluromethanesulfonic acid and toluenesulfonic acid, in a reaction zone wherein the molecular ratio of said dicarboxylic acid and hydrogen peroxide is within the range of from 1:2 to about 1:5, whereby there is formed a reaction slurry in said reaction zone, the amount of phosphoric acid employed being sufficient to provide an easily stirrable reaction mixture and to predissolve the dicarboxylic acid reactant at temperatures between about 60°–100° C.; maintaining the reaction slurry in an agitated condition; maintaining the temperature of the reaction slurry within the range of from about 20° to about 70° C. during the reaction period and thereafter separating the diperoxydicarboxylic acid from the reaction slurry.

20. Process of claim 19 wherein the stronger acid is sulfuric acid.

21. Process of claim 19 wherein the stronger acid is methanesulfonic acid.

22. Process of claim 19 wherein the stronger acid is trifluoromethanesulfonic acid.

23. Process of claim 19 wherein the stronger acid is toluenesulfonic acid.

24. Process of claim 19 wherein the hydrogen peroxide concentration is within the range of from about 30 to about 90%.

25. Process of claim 24 wherein the hydrogen peroxide has a concentration of at least about 65%.

26. Process of claim 19 wherein the molecular ratio of dicarboxylic acid and hydrogen peroxide is within the range of from about 1:3 to about 1:4.

27. Process of claim 19 wherein the phosphoric acid concentration is within the range of from about 70 to about 100%.

28. Process of claim 27 wherein the phosphoric acid has a concentration within the range of from about 85 to about 95%.

29. Process of claim 19 wherein the molecular ratio of dicarboxylic acid and phosphoric acid is within the range of from about 1:6 to about 1:15.

30. Process of claim 29 wherein the molecular ratio of the dicarboxylic acid and phosphoric acid is within the range of from about 1:8 to about 1:12.

31. Process of claim 19 wherein the dicarboxylic acid is dissolved in the phosphoric acid reaction medium prior to being brought together and reacted with the hydrogen peroxide.

32. Process of claim 19 wherein the dicarboxylic acid reactant is azelaic acid.

33. Process of claim 19 wherein the dicarboxylic acid reactant is dodecanedioic acid.

34. A process for preparing a saturated $C_{12}$–$C_{16}$ aliphatic diperoxydicarboxylic acid which comprises the steps of bringing together and reacting, a saturated $C_{12}$–$C_{16}$ aliphatic dicarboxylic acid and hydrogen peroxide having a concentration within the range of from about 30 to about 90%, in a phosphoric acid reaction medium containing up to about 5% by weight of the phosphoric acid selected from the group consisting of sulfuric acid, methanesulfonic acid, trifluromethanesulfonic acid and toluenesulfonic acid of a stronger acid, in a reaction zone, wherein the molecular ratio of said dicarboxylic acid and hydrogen peroxide is within the range of from about 1:2 to about 1:5, the phosphoric acid having a concentration within the range of from about 70 to about 100%, the molecular ratio of dicarboxylic acid and phosphoric acid being within the range of from about 1:6 to about 1:15, whereby there is formed a reaction slurry in said reaction zone; maintaining the reaction slurry in an agitated condition; maintaining the temperature of the reaction slurry within the range of from about 20° to about 70° C. and thereafter separating the diperoxydicarboxylic acid from the reaction slurry.

35. Process of claim 34 wherein the stronger acid is sulfuric acid.

36. Process of claim 34 wherein the stronger acid is methanesulfonic acid.

37. Process of claim 34 wherein the stronger acid is trifluoromethanesulfonic acid.

38. Process of claim 34 wherein the stronger acid is toluenesulfonic acid.

39. Process of claim 34 wherein the hydrogen peroxide has a concentration of at least about 65%.

40. Process of claim 34 wherein the phosphoric acid has a concentration within the range of from about 85 to about 95%.

41. Process of claim 34 wherein the molecular ratio of dicarboxylic acid to phosphoric acid is within the range of from about 1:8 to about 1:12.

42. Process of claim 34 wherein the dicarboxylic acid is dissolved in the phosphoric acid reaction medium prior to being brought together and reacted with the hydrogen peroxide.

43. Process of claim 34 wherein the dicarboxylic acid reactant is azelaic acid.

44. Process of claim 34 wherein the dicarboxylic acid reactant is dodecanedioic acid.

* * * * *

UNITED STATES PATENT AND TRADEMARK OFFICE
CERTIFICATE OF CORRECTION

PATENT NO. : 4,147,720

DATED : April 3, 1979

INVENTOR(S) : Sidney Berkowitz

It is certified that error appears in the above-identified patent and that said Letters Patent are hereby corrected as shown below:

Column 1, line 16, "path" should read --part--; column 1, line 18, "and the" should read --the--. Column 3, line 66, "preferred" should read --the preferred--. Column 5, line 6, "removed" should read --remove--; column 5, line 26, "0.02" should read --0.20--. Column 7, line 15, "In" should read --At--. Column 9, line 33, Claim 34, "of a stronger acid" should be moved to line 31 after phosphoric acid.

Signed and Sealed this

Twenty-first Day of August 1979

[SEAL]

Attest:

Attesting Officer

LUTRELLE F. PARKER

Acting Commissioner of Patents and Trademarks